(12) United States Patent
Mehta

(10) Patent No.: US 8,834,433 B2
(45) Date of Patent: *Sep. 16, 2014

(54) NASAL RINSE TIP

(71) Applicant: Ketan C. Mehta, Santa Rosa, CA (US)

(72) Inventor: Ketan C. Mehta, Santa Rosa, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/708,681

(22) Filed: Dec. 7, 2012

(65) Prior Publication Data

US 2013/0197450 A1    Aug. 1, 2013

Related U.S. Application Data

(63) Continuation of application No. 12/567,518, filed on Sep. 25, 2009, now Pat. No. 8,343,114.

(51) Int. Cl.
*A61M 31/00* (2006.01)
*A61M 3/02* (2006.01)

(52) U.S. Cl.
CPC ............ *A61M 3/0262* (2013.01); *A61M 3/025* (2013.01); *A61M 3/0279* (2013.01); *A61M 2210/0618* (2013.01)
USPC ........................................................ 604/275

(58) Field of Classification Search
USPC ................ 604/275, 516, 23, 24, 26, 187, 212
See application file for complete search history.

(56) References Cited

U.S. PATENT DOCUMENTS

| | | | | |
|---|---|---|---|---|
| 2,135,052 A | * | 11/1938 | Rose | 604/24 |
| 3,186,645 A | * | 6/1965 | Eberlein | 239/567 |
| 3,471,092 A | * | 10/1969 | Hickey | 239/579 |
| 5,116,311 A | * | 5/1992 | Lofstedt | 604/516 |
| 5,806,723 A | | 9/1998 | DuBose | |
| 5,906,198 A | | 5/1999 | Flickinger | |
| 6,520,384 B2 | | 2/2003 | Mehta | |
| 6,644,305 B2 | * | 11/2003 | MacRae et al. | 128/200.21 |
| 7,302,948 B2 | * | 12/2007 | Anderson | 128/200.14 |
| 2002/0158089 A1 | | 10/2002 | Mehta | |
| 2004/0068222 A1 | * | 4/2004 | Brian | 604/65 |
| 2005/0210572 A1 | | 9/2005 | Fogel | |
| 2008/0008979 A1 | | 1/2008 | Thomas et al. | |
| 2008/0154183 A1 | | 6/2008 | Baker et al. | |
| 2008/0312674 A1 | | 12/2008 | Chen et al. | |
| 2009/0281454 A1 | | 11/2009 | Baker et al. | |

(Continued)

FOREIGN PATENT DOCUMENTS

| | | |
|---|---|---|
| JP | 2005-287669 A | 10/2005 |
| KR | 10-2000-0066190 | 11/2000 |
| WO | WO 02/07668 A1 | 1/2002 |

OTHER PUBLICATIONS

Ocean Complete® [online]. Fleming Pharmaceuticals, 2009 [retrieved on Dec. 29, 2009]. Retrieved from the Internet: <URL: http://flemingpharma.com/content/view/141/140/, 2 pages.

(Continued)

*Primary Examiner* — Aarti B Berdichevsky
*Assistant Examiner* — Bradley Osinski
(74) *Attorney, Agent, or Firm* — Fish & Richardson P.C.

(57) ABSTRACT

A device for nasal lavage is described. The device ejects a gentle flow of fluid under pressure. The fluid stream provides a high quantity of fluid at low pressure. The low pressure fluid stream is more comfortable for a user than a high pressure fluid stream that is delivered by some types of pressurized cans of solution.

26 Claims, 8 Drawing Sheets

(56) References Cited

U.S. PATENT DOCUMENTS

| | | |
|---|---|---|
| 2011/0077603 A1 | 3/2011 | Mehta |
| 2011/0144588 A1 | 6/2011 | Taylor et al. |
| 2011/0155750 A1 | 6/2011 | Bernstein et al. |
| 2012/0277675 A1 | 11/2012 | Mehta |

OTHER PUBLICATIONS

Ocean Ultra® Sterile Saline Nasal Mist [online]. Fleming Pharmaceuticals, 2009 [retrieved on Dec. 29, 2009]. Retrieved from the Internet: <URL: http://flemingpharma.com/content/view/84/81/, 1 page.

SinuCleanse Squeeze™ [online]. Med-Systems, Inc., 2008 [retrieved on Dec. 29, 2009]. Retrieved from the Internet: <URL: http://www.sinucleanse.com/product/squeeze.htm, 3 pages.

Authorized Officer Ji Myong Nho, International Search Report and Written Opinion in PCT/US2010/050434, mailed Jun. 21, 2011, 9 pages.

Authorized officer Agnes Wittmann-Regis, International Preliminary Report on Patentability in PCT/US2010/050434, mailed Apr. 5, 2012, 6 pages.

Authorized officer Cheol Soo Lee, International Search Report and Written Opinion in PCT/US2012/035616, mailed Nov. 26, 2012, 9 pages.

Authorized officer Philippe Bécamel, International Preliminary Report on Patentability in PCT/US2012/035616, mailed Nov. 7, 2013, 6 pages.

* cited by examiner

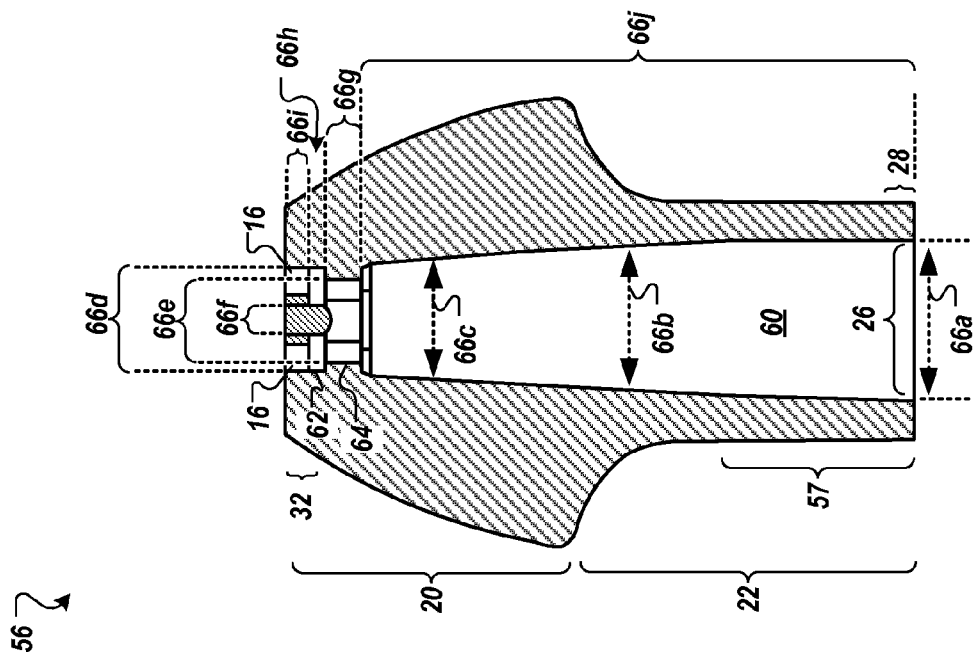
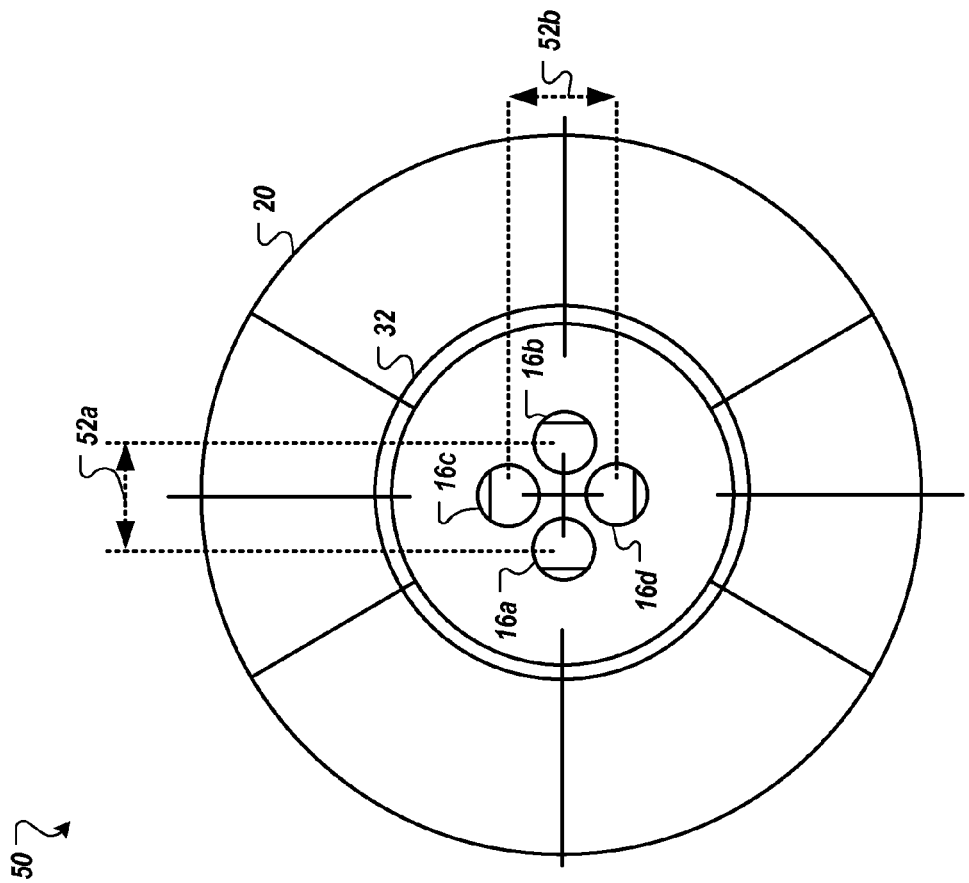

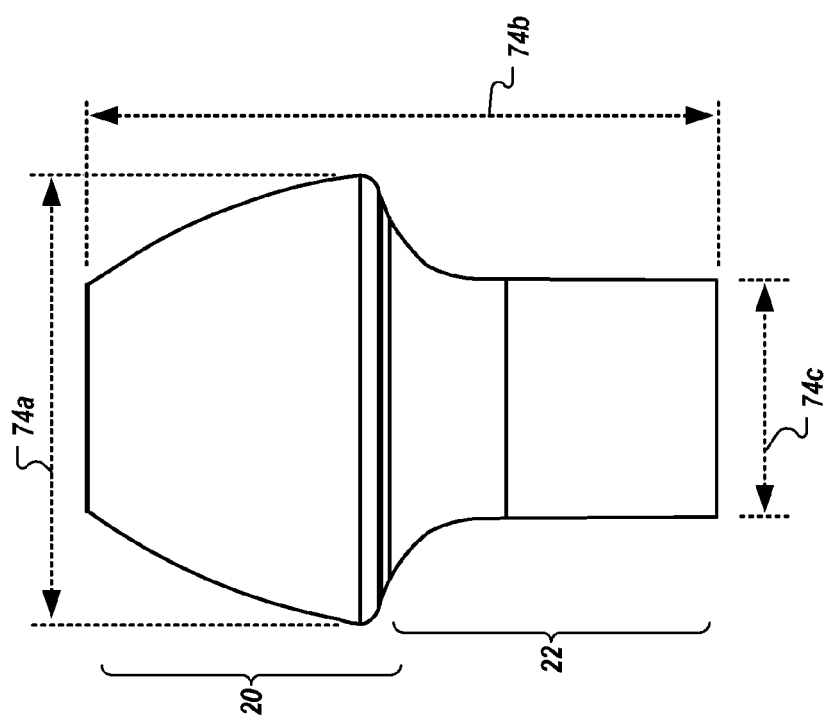

NASAL RINSE TIP

BACKGROUND

This invention relates to nasal lavage.

People in many parts of the world perform nasal cleansing (or nasal irrigation) using a neti pots or other products on a routine basis, like brushing their teeth or showering. Nasal cleansing is even incorporated into some forms of yoga practice, such as in Jala neti. Jala neti is a Sanskrit term that refers to cleansing and means "water cleansing." Often, the solution for rinsing the nasal passages using a neti pot or other product is a saline solution. Some people use nasal rinsing to reduce allergies, improve breathing, eliminate post-nasal drip or sinus infections, moisten dry nasal passages, avoid catching a cold or to generally improve one's health. Some people also claim that nasal lavage improves ones vision by cleaning the tear ducts, improves the sense of smell and improves ones sense of taste.

Some problems with nasal lavage products can be that the canisters containing rinse solution may be under excessive pressure, causing solution flow to be somewhat uncomfortable during use.

SUMMARY

The device described herein is configured for ease of use, controllability of the solution exiting the device, and comfort for the user.

In one aspect, a device is described that ejects fluid. The device includes a body surrounding a chamber, wherein the body is configured to resist a change in shape when a pressure change occurs within the body, a valve, an actuator having a fluid path that is fluidly connected to the chamber when the valve is in an open position and a tip, wherein the tip is configured to attenuate a pressure of fluid flow exiting the actuator.

Embodiments of the device can include one or more of the following features. A tube can be within the chamber and connected to the valve. The device can include a bag, wherein the bag comprises a flexible material, is within the body, and surrounds the tube and an interior of the bag is hermetically sealed from a space between the body and an exterior of the bag. The tip can be formed of a flexible material. The tip can be formed of silicone. The actuator can be formed of a material that is more rigid than the tip. The tip can have a distal portion and a proximate portion, an aperture in the proximate portion defines an interior of a collar that surrounds a portion of the actuator, the distal portion has one or more apertures and a stop, the stop of the tip can be positioned to block the fluid flow exiting the aperture and causes the fluid flow to be redirected toward the proximate portion of the tip. The tip can have an exterior circumference of less than 1.5 cm. The device can have one or more apertures in the distal portion include at least four apertures and the at least four apertures surround the stop. The device can have a canal between the aperture that defines an interior of the collar and the stop tapers inwardly from the collar to the stop. The exterior of the tip can taper outwardly between the distal portion and the proximate portion. The exterior can be curved between the distal portion and the proximate portion. The device can include a sterile saline solution within the body, wherein when the body is held in an upright orientation with the tip furthest from ground and no obstructions are beyond the tip to affect the fluid flow, actuating the actuator causes the fluid flow to exit the actuator and exit the tip in a stream, wherein an entirety of the stream projects up and away from the tip and curves back toward the ground within 6 centimeters of the tip, without the tip the fluid flow exits the actuator in a stream that extends away from the actuator along a substantially straight and unchanging trajectory at 6 centimeters from the actuator. A canal can be between the at least four apertures and the aperture that defines the interior of the collar and each of the four apertures is fluidly connected to an annular chamber, and the annular chamber is fluidly connected to the canal. A greatest extent of the at least four apertures together can be greater than an external circumference of the annular chamber. The device can include a circular chamber between the canal and the annular chamber. The external circumference of the annular chamber can be greater than a circumference of the circular chamber. The circumference of the circular chamber can be less than a minimum circumference of the canal by at least 0.1 mm. The canal can have an internal volume of at least 0.47 cm$^3$. An area of the apertures in the distal portion of the tip can be greater than an area of the circular chamber. The tip can have one or more grooves extending from an open proximal portion and at least 50% of a length of the tip. The tip can have an aperture along a side surface of the tip that is fluidly connected to an interior channel extending from the open proximal portion. The tip can have two apertures across from one another, the apertures and the interior channel configured in the shape of a T.

The devices described herein may include one or more of the following advantages. A gentle flow of solution can be expelled from a soft or compliant tip. The tip material can be comfortable against a user's nose. The gentle flow can be used to irrigate or cleanse a tissue, such as the interior of a nostril. The gentle flow of fluid can be less irritating or painful than a more intense stream of fluid. A user is more likely to use a gentle flow of fluid and treatment compliance can be higher. This can result in a more effective treatment of the patient.

The details of one or more implementations of the invention are set forth in the accompanying drawings and the description below. Other features, objects, and advantages of the invention will be apparent from the description and drawings, and from the claims.

DESCRIPTION OF DRAWINGS

FIGS. 2 and 3 are a schematic top view and a schematic plan view of a tip used on the device.

FIG. 6 is a schematic side view of the tip.

Like reference symbols in the various drawings indicate like elements.

DETAILED DESCRIPTION

Figure 1:
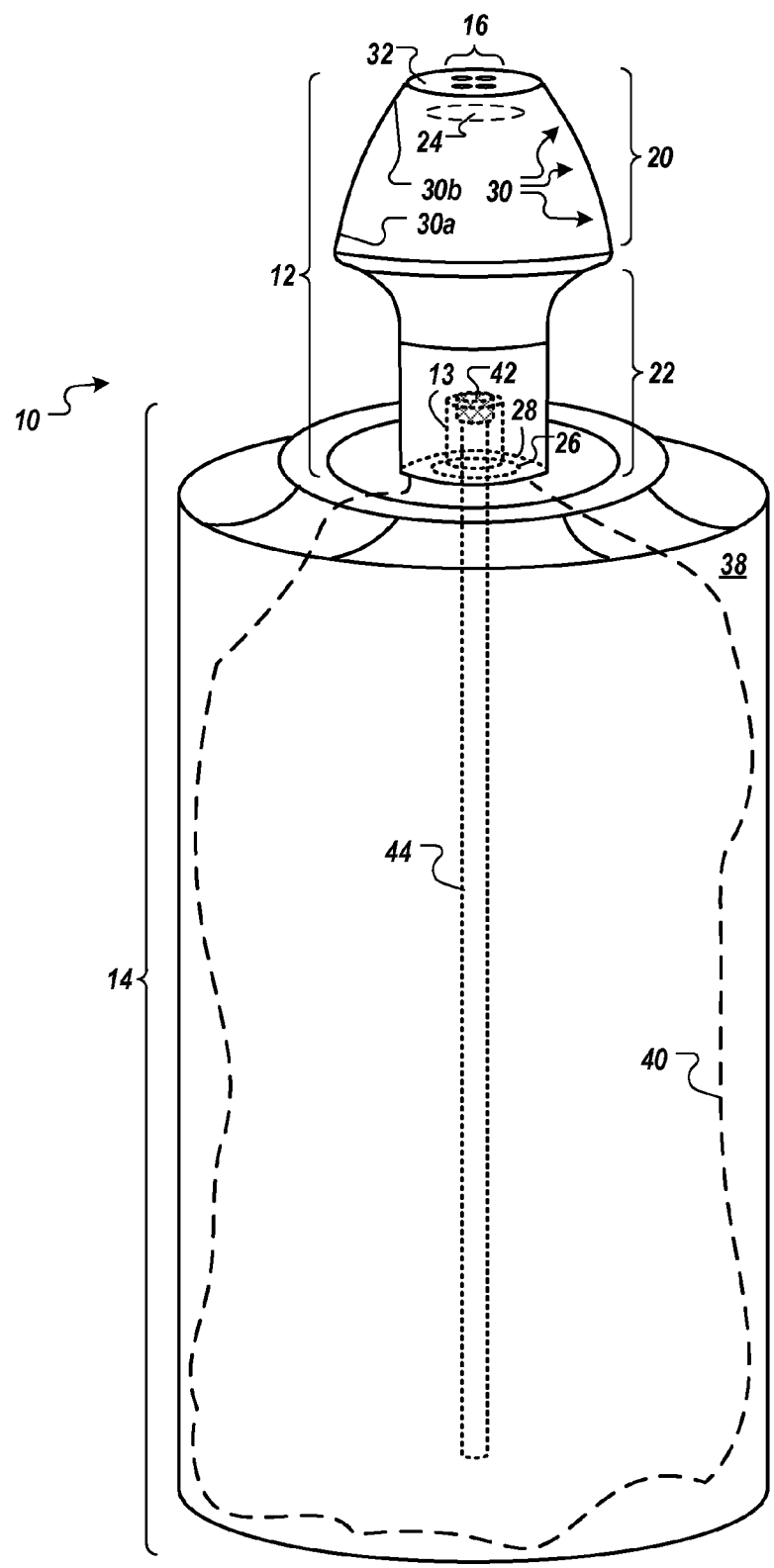
FIG. 1 is a schematic perspective view of a device.

Referring to FIG. 1, a fluid ejection device 10 is shown. The fluid ejection device 10 includes a tip 12 that is attached to an actuator 13, which in turn is attached to a body 14. The body 14 can be, for example, a container of saline solution or any other fluid suitable for irrigating nasal cavities. The fluid ejection device 10 can be used, for example, to provide nasal rinsing (or irrigation or nasal lavage), such as to treat allergies, improve breathing, eliminate post-nasal drip or sinus infections, moisten dry nasal passages, etc. The tip 12 can attenuate the pressure of fluid stored in the body 14, dispensing fluid at a significantly more gentle pressure but at a higher volume or flow rate. The gentle pressure can be sufficient pressure to delivery a flow of fluid to nasal tissue without the pressure being so great as to apply sufficient pressure to the tissue to displace the tissue.

In some implementations, the body 14 can be a fluid container (e.g., can, canister, bottle, etc.) having bag-on valve technology where there is a bag inside the can and the valve can release the solution when the actuator is actuated, i.e., pressed. In some implementations, the fluid ejection device 10 can be used on a plastic bottle which is pressurized and has a solution inside the bottle. In some implementations, the fluid delivery is from an aerosol type can, but the fluid is ejected from the tip 12 in a fluid stream, rather than an aerosol.

The tip 12 can be operable to provide an attenuated pressure of fluid flow from the body 14. For example, the body 14 can be a commercially-available, pressurized container of saline solution or other sterile fluid which ordinarily dispenses fluid at a pressure that may be unsuitable, uncomfortable or unsafe for use in nasal lavage. As such, the tip 12 can include features that facilitate the delivery of fluid in a generally more gentle stream through at least one (e.g., about four or more) apertures 16 at the end of the tip 12. Fluid flow can be controlled, for example, by pressing the tip 12. In some implementations, the tip 12 can be pressed straight against the nose, allowing fluid to flow from the tip. In other implementations, pressing the tip 12 from the side can control fluid flow.

The tip 12 includes a distal portion 20 and a proximate portion 22. The distal portion 20 of the tip 12 can be approximately conically shaped, with a convex curved surface leading from the apertures 16 toward the proximate portion 22. In other implementations, the distal portion 20 can be approximately gumdrop- or mushroom-shaped. The tip 12 can include a tapered surface 30 that permits the tip 12 to conform to nostrils of different sizes. Specifically, the exterior of the tip 12 can be tapered outwardly along the distal portion 20. In other words, the tip 12 tapers from a wide portion 30*a* up to a narrow portion 30*b*, where the narrow portion 30*b* is closer to the apertures 16 than to the proximate portion 22. Moreover, the tip 12 can be sized to prevent the wide portion 30*a* from extending all the way into the user's nostril.

The distal portion 20 can contain the features of the tip 12 that facilitate fluid flow, at an attenuated pressure, from the apertures 16. A stop 24 can be the ceiling of the interior fluid canal within the tip 12, positioned to block the fluid flow exiting the body 14, and causing the fluid flow to be redirected toward the proximate portion 22 of the tip 12. As a result, fluid can "pool" or otherwise accumulate inside the tip 12 and be dispensed at a reduced pressure through the apertures 16, while being replenished from fluid from the body 14 which dispenses at a higher pressure.

The apertures 16 can be arranged, for example, on a mesa 32 at the end of the distal portion 20. As depicted, the mesa 32 has a relatively flat surface, but other shapes (e.g., a convex shape) can be used that are effective at distributing the apertures 16 for efficient dispensing of fluid.

An aperture 26 in the proximate portion 22 can define the interior boundary of a collar 28 that surrounds, and securely attaches to, a portion of the actuator 13. In some implementations, if the actuator 13 is relatively small (e.g., a spray-paint can's spray button size), the aperture 26 can attach directly to the body 14. For example, the collar 28 can provide a snap-fit, screw-fit, or other such sealed connection between the proximate portion 22 (of the tip 12) and the body 14. However, when the actuator 13 is significantly larger, as it can be in some implementations, the tip 12 can attach directly to the actuator 13. In general, the tip 12 can be manufactured in various sizes or be adjustable to fit any size actuator 13 or body 14.

To aid in comfort of use, the tip 12 can be formed of a flexible material, such as silicone or some another soft, flexible material (e.g., plastic, rubber, non-permeable cloth, etc.) that can generally feel comfortable against the user's skin. The tip 12 can have an exterior circumference of less than 2 cm, such as less than 1.5 cm, allowing it to fit snugly against, but not extend all the way into, an average sized user's nostril. The actuator 13 can be formed of a material that is significantly more rigid than the tip 12. As such, the actuator 13 can hold its shape during use.

The body 14 surrounds a chamber 38. The body 14 can be configured to resist a change in shape when pressure changes occur within the body 14 due to the contents of the chamber 38. For example, if the body 14 is formed of a generally rigid material (e.g., metal, such as steel or aluminum, plastic, such as a recyclable resin, such as polyethylene, polycarbonate or polypropylene, etc.), the body 14 can retain its shape when the chamber 38 is fully-pressurized (e.g., full of fluid), partially-pressurized, and essentially un-pressurized (e.g., when the fluid is essentially depleted).

In some implementations, the body 14 can include a bag 40 inside the chamber 38. The bag 40 can contain the fluid stored by the body 14 and can be formed of a flexible material, such as a pliable plastic. Further, the bag 40 can be hermetically sealed from the space between the body 14 and an exterior of the bag 40. As a result, using the bag 40 or a device similar to the bag-on valve technology (e.g., a pressurized can or pressurized bottle) can provide a sterile solution suitable for use in a body cavity or with a wound.

As will be described in more detail below, the body 14 can include a valve 42 and a tube 44. The valve 42, such as any type of valve used on spray cans, can be used to control (e.g., start, stop, etc.) the flow of fluid from the chamber 38 to the tip 12. The fluid can flow through the tube 44 which can extend into the bottom end of the body 14, or the end that is most distal from the tip 12.

Referring to FIG. 2, an exemplary top view 50 of the fluid ejection device 10 is shown. The top view 50 shows the apertures 16*a*-16*d* arranged on the mesa 32, located on the tip of the distal portion 20. As depicted in FIG. 2, in some implementations, the centers of any pair of adjacent apertures 16*a*-16*d* are spaced at between about 1 and 4 millimeters, such as about 3 millimeters, as shown by distances 52*a* and 52*b*. Specifically, the distance 52*a* corresponds to the distance between the centers of apertures 16*a* and 16*b*. Similarly, the distance 52*b* corresponds to the distance between the centers of apertures 16*c* and 16*d*. The tip 12 can have an exterior circumference of less than 1.5 cm.

The diameters of the apertures 16*a*-16*d* can be any value (e.g., between about 1 and 2 millimeters, such as about 1.5 millimeters) such that, for example, the combination of the group of apertures 16*a*-16*d* produces a sufficient stream when the fluid ejection device 10 is in use. In some implementations, as the number of apertures is increased, the diameter of the apertures generally can be reduced.

In some implementations, different sizes of the apertures 16*a*-16*d* and/or other spacing between the apertures 16*a*-16*d* can be used, and fewer or additional apertures 16*a*-16*d* can exist, with varying distances between any of the apertures 16*a*-16*d*. In some implementations, distances 52*a* and 52*b* may be less than, or greater than, 3 millimeters. In some implementations, there are two, three, four, five or six apertures in the tip 12. The total cross sectional area of the apertures 16a-16d is generally less than the cross sectional area at any cross section of the canal 60 (e.g., having diameters 66 described with respect to FIG. 3) carrying the supply of fluid through the tip 12.

Referring to FIG. 3, an exemplary side cross-section view 56 of the fluid ejection device 10 is shown. The view 56 shows the tapered shape of the tip 12, including the tapered surface 30 that extends along the distal portion 20 toward its intersection with the proximate portion 22. The view 56 further shows a cross-section of the features of the interior of the tip 12.

Fluid can flow through the tip 12 by entering a base area 57. For example, the base area 57 can include the collar 28 that serves as the connection point between the tip 12 and the actuator 13 and some adjacent region of the tip 12, such as a lower third of the tip. The collar 28 can surround or fit over a portion of the actuator 13, such as the portion of the actuator 13 from which fluid can flow. Fluid dispensed from within the chamber 38 can flow through the base area 57 and through the interior of the tip 12, exiting through the most distal end of the distal portion 20. In some implementations, the fluid can flow through the tube 44 and valve 42 (see FIG. 1).

The view 56 further shows internal features of the tip 12. A canal 60 in the interior of the tip can provide fluid connectivity between the chamber 38 (e.g., via the actuator) and the apertures 16. Specifically, the canal 60 can extend from (and define the shape of) the aperture 26, defining the interior of the collar 28. The canal can extend to and be fluidly connected to an annular 62. In some implementations a circular or cylindrical chamber 64 can exist, and be fluidly attached to, annular chamber 62 and canal 60. The canal 60 and the chambers 62 and 64 can work in combination, for example, based on their dimension, to attenuate the pressure of the fluid received from the body 14 that flows through and exits the tip 12. For example, the fluid entering the tip 12 can generally pool within the canal 60, and the chambers 62 and 64 can facilitate the flow of the fluid through the tip 12 at suitable pressure through the apertures 16. For instance, the shape and size of the chambers 62 and 64 can restrict the flow of fluid to a volume that is ideal for delivery to the apertures 16.

Various dimensions of components of the tip 12 can exist. For example, the canal 60 can have a tapered shape, having dimensions that include, for example, a diameter 66a of in the range between about 5 and 9 mm, such as about 7 mm at the aperture 26, a diameter 66b of in the range between about 5 and 7 mm, such as about 6 mm roughly halfway up through the canal 60, and an even smaller diameter 66c such as in the range between about 4 and 6 mm, such as about 5.5 mm or less approaching the apertures 16. The annular chamber 62 can have, for example, an outer diameter 66d equal to or less than 66c, such as in the range between about 4 and 5.2 mm, such as about 4.6 mm and an inner diameter 66f of in the range between about 1 and 1.5 mm, such as about 1.3 mm. The circular chamber 64 can have a diameter 66e equal to or less than that of diameter 66c in the range between about 3 and 5 mm, such as about 3.7 mm. In some implementations, the diameter 64 is less than the outer diameter of chamber 62. The diameters 66a-66f are just examples, as other diameters can be used in other implementations.

Various other dimensions of components of the tip 12 can exist. For example, the circular chamber 64 can have a thickness 66g in the range between about 1 and 2 mm, such as about 1.5 mm. The annular chamber 62 can have a thickness 66h in the range between about 0.5 and 1.2 mm, such as about 0.8 mm. The region between the mesa 32 and the stop 24 at the end of the distal portion 20 can have a thickness 66i in the range between about 0.8 and 1.2 mm such as about 1 mm. The canal 60 can have a length 66j in the range of between about 20 and 30 mm, such as about 25 mm. These thicknesses and lengths can vary in other implementations; however the side wall integrity of the tip 12 needs to be maintained.

Internal features of the tip 12 can vary in size and proportion to each other, the advantages of which can include better control of pressure attenuation. For example, in some implementations, the external circumference of the annular chamber 62 can be greater than the circumference of the circular chamber 64. In some implementations, the greatest extent of the apertures 16 (e.g., the sum of the surface areas of the apertures 16) can be greater than an external circumference of the annular chamber 62. In some implementations, the circumference of the circular chamber 64 is less than the minimum circumference of the canal 60 by in the range between 0.5 mm and 1.5 mm, such as at least about 0.1 mm. In some implementations, the canal 60 can have an internal volume of in the range between 0.3 cm$^3$ and 0.5 cm$^3$, such as at least about 0.4 cm$^3$. In some implementations, the combined area of the apertures 16 in the distal portion 20 of the tip 12 can be greater than an area of the circular chamber 64.

In some implementations, the total cross sectional area of apertures 16 is greater than the cross sectional area of the valve 42. Without being bound to any particular theory, liquid exits from chamber 38 at a high pressure, such as at a pressure greater than about 10 psi, such as in the range of 20 and 200 psi, such as at a pressure of greater than about 30 psi and enters canal 60 directed toward the apertures 16. The high pressure fluid contacts an end wall (e.g., the stop 24), which redirects the fluid toward aperture 26. Some fluid exits apertures 16 while canal 60 fills with fluid. Once the canal 60 fills, because the overall effective area of the apertures 16 area is greater than the valve 42 exit area in combination with the availability of fluid in the canal 60, the pressure of fluid exiting the chamber 38 is attenuated and the fluid exits the apertures 16 in a gentle contiguous stream.

Figure 4:
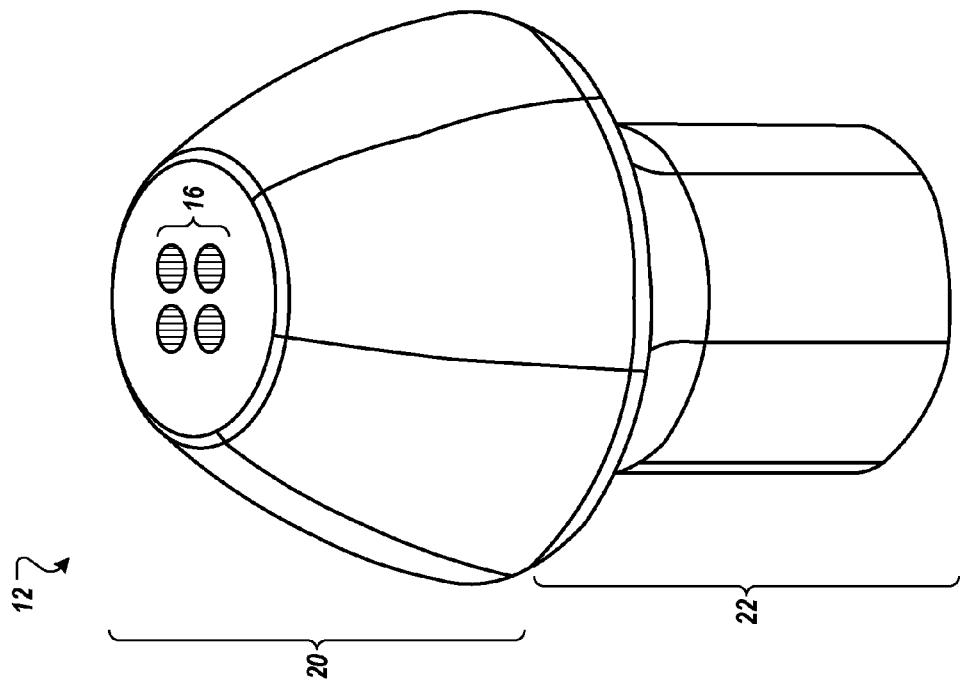

Referring to FIG. 4, a perspective view of the fluid ejection device 10 is shown. Although the implementation shown in FIG. 4 includes four apertures 16 of the same size, other implementations can include more (or fewer) of the apertures 16. Further, the apertures 16 can have various sizes and spacing, for example, as can be determined through experimentation to deliver a stream of fluid more suitable for nasal lavage.

In some implementation, various models of the fluid ejection device 10 can exist, each having the advantage of a different configuration of apertures 16. For example, some users may prefer using a specific "Model X" over "Model Y" because of a difference in operation or "feel" of each, such as a noticeable difference in the strength of the stream of fluid from each. In some implementations, additional versions of the fluid ejection device 10 can have significantly larger tips 12 (e.g., for adults with significantly larger nostrils) or significantly smaller tips 12 (e.g., for babies or toddlers). As such, different models or versions of the fluid ejection device 10 can be produced.

Although implementations of the tip 12 and the fluid ejection device 10 are generally intended for human use, other implementations can include models or versions that are intended to use for animals, such as pets or livestock.

Figure 5:
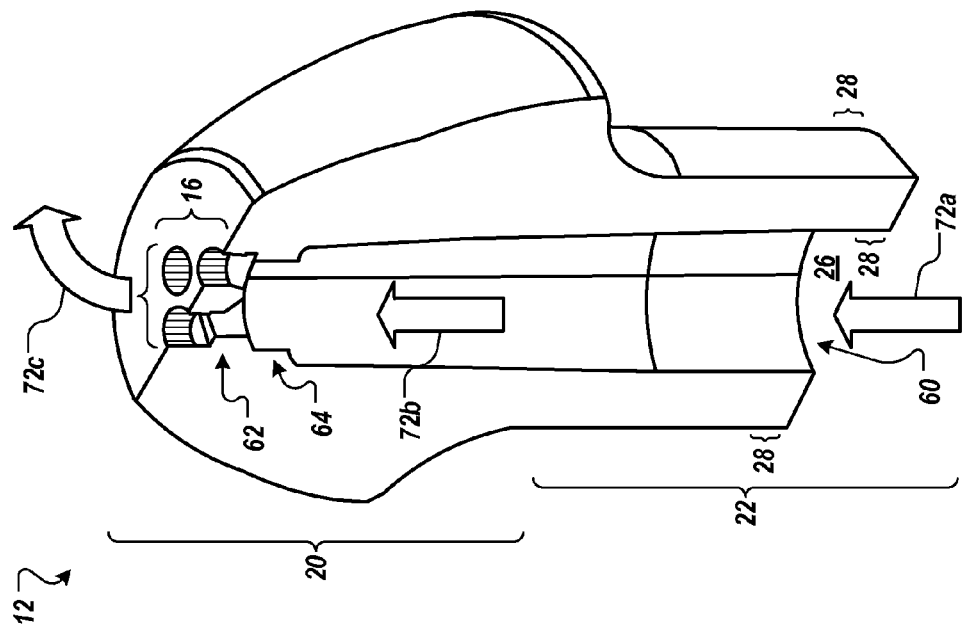
FIGS. 4 and 5 are schematic perspective views of a tip used on the device.

Referring to FIG. 5, a cross-section of a perspective view of the fluid ejection device 10 is shown. The view shows half of the tip 12 exposed, and as such exposes half of the distal portion 20 and the proximate portion 22, as well as revealing the canal 60.

Fluid can flow through the tip 12 in the direction indicated by arrows 72a-72c. Specifically, fluid from the body 14 can enter the tip 12, as indicated by arrow 72a. Fluid entering the tip 12 does so through the aperture 26, as defined by the inner dimension of the collar 28. Fluid flows through the canal 60, on the interior of the tip 12, as indicated by arrow 72c. Fluid exits the tip 12 at the apertures 16, as indicated by arrow 72c. Before reaching the apertures 16, the fluid can flow through the annular chamber 62, the circular chamber 64, and any other chambers not depicted.

Referring to FIG. 6, exemplary dimensions of the tip 12 are shown. For instance, in some implementations, the diameter 74a of the widest part of the distal portion 20 (and of the tip 12 itself) can be, for example, in the range between 15 and 25 mm, such as about 20 mm or any other size that is suitable for use with human nostrils. In some implementations, the length 74b of the tip 12 can be, for example, in the range between 20 and 40 mm, such as about 30 mm, or any other suitable length. For instance, longer tips 12 can be necessary to fit different types of actuators 14, depending on the size of any exposed tube 44 and valve 42. The diameter 74c of the proximate portion 22 of the tip 12 can be, for example, in the range between 7 and 14 mm, such as about 10 mm, or any other size that can enable the tip 12 to fit the portion of the actuator 13 or body 14 to which the tip 12 is attached.

Figure 7:
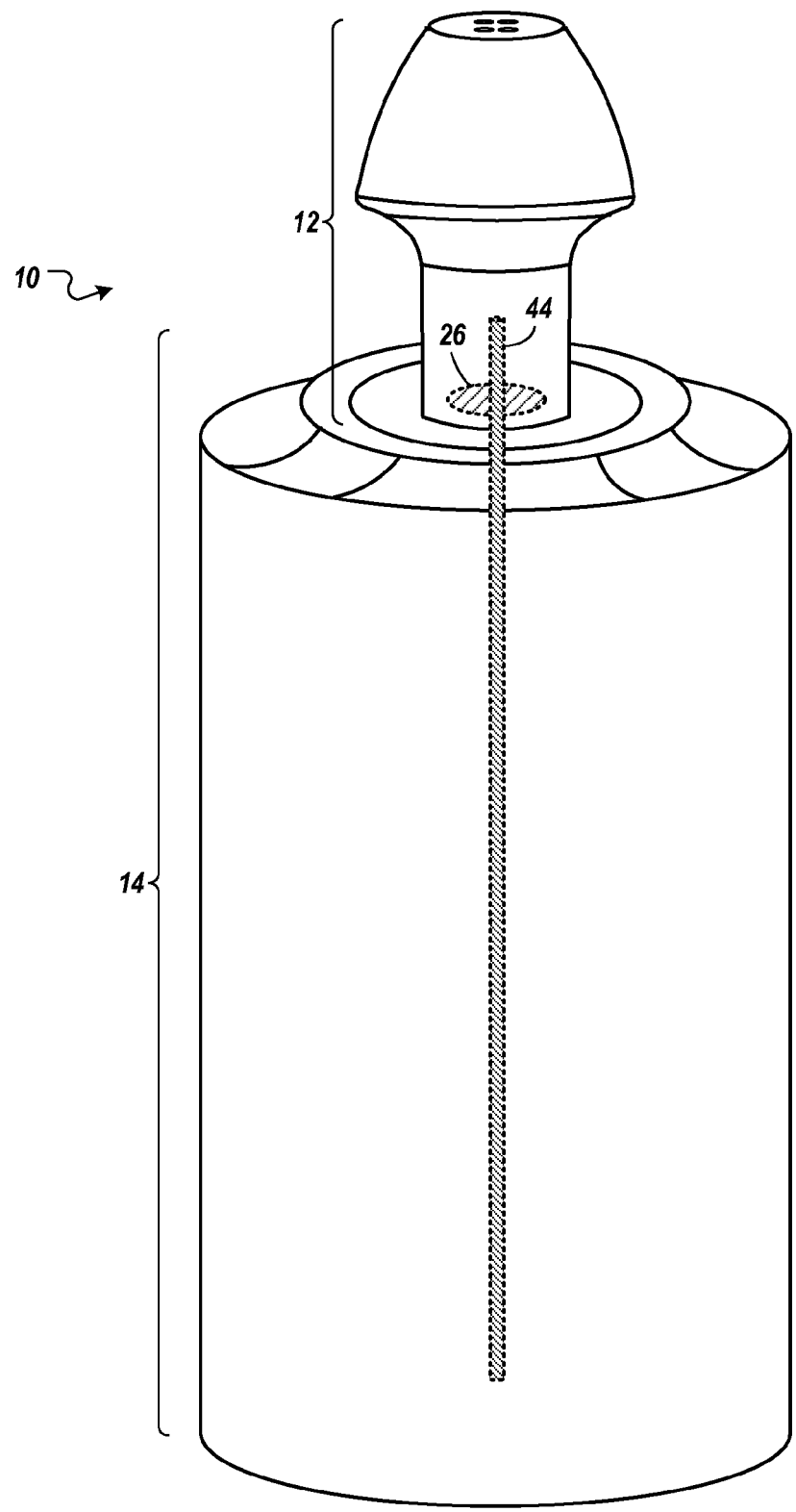
FIG. 7 is a schematic perspective view of the device.

Referring to FIG. 7, the fluid ejection device 10 is shown with the tip 12 covering the aperture 26 and the valve 42 which are both extruding from the body 14.

Figure 8:
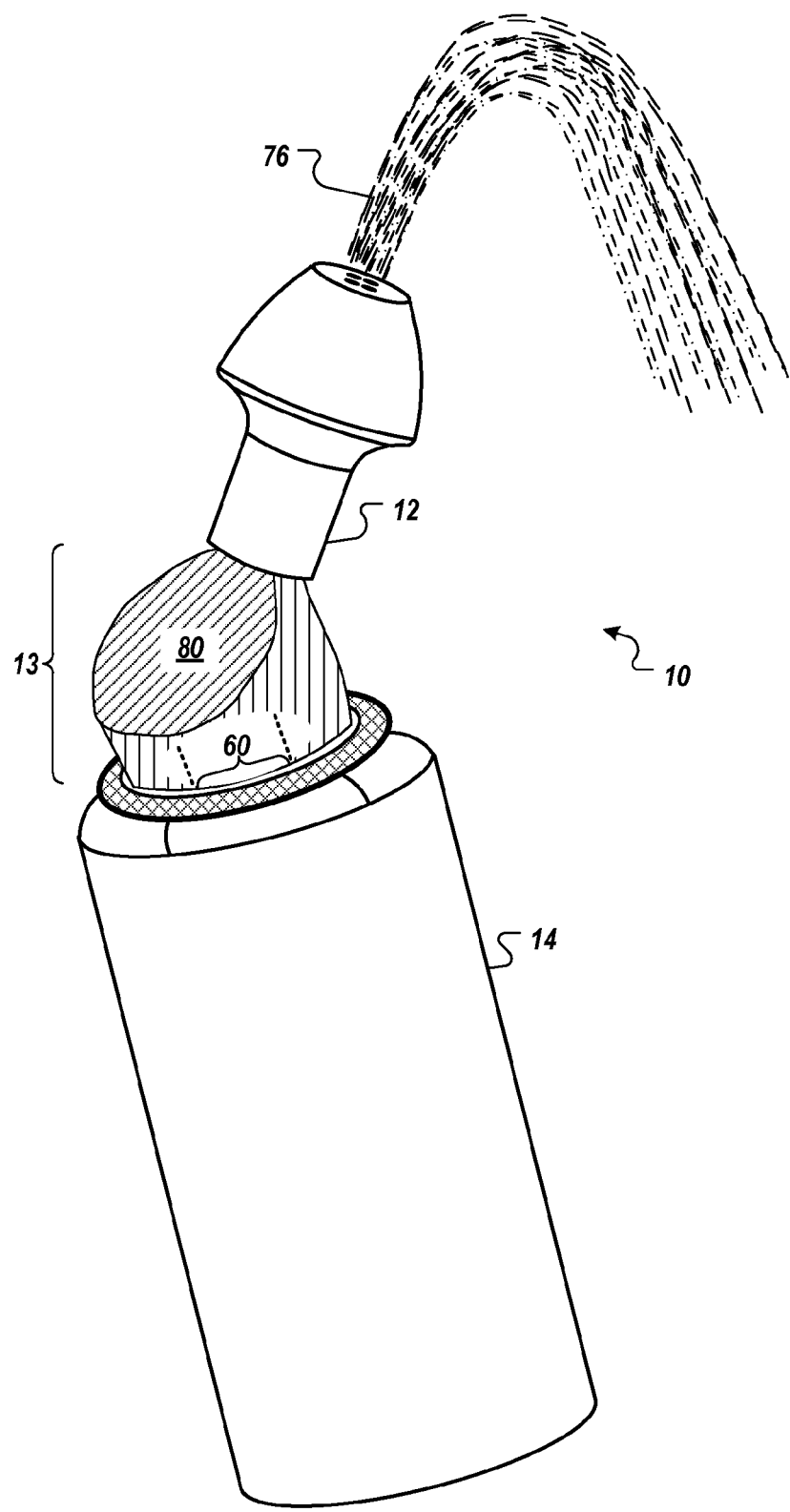
FIG. 8 is a schematic perspective view of the device in use.

Referring to FIG. 8, an exemplary stream of fluid 76 flowing from the fluid ejection device 10 is shown. The stream of fluid 76 can have a gentle arc, as depicted, due to the pressure-attenuating features of the tip 12. For example, while the fluid in the body 14 may be stored and released at a generally high pressure (e.g., too forceful for nasal lavage), the tip 12 can receive the fluid at high pressure, attenuate the pressure, and dispense the fluid at a lower pressure, but having a higher volume. In this way, the fluid stream can achieve an arc and flow as generally depicted by the stream of fluid 76. The stream of fluid 76 can exit the tip 12 along a trajectory that is along a central axis of the canal 60. The apex of the arc of fluid occurs within a range of between about 4 and 12 cm, such as 8 cm, such as within 7 cm or within 5 cm of the apertures. In some implementations, fluid is ejected in a stream rather than ejected as a mist or as individual droplets.

In some implementations, the tip 12 can include, or be fluidly connected to, the actuator 13 that can be used to start and stop the flow of fluid from the body 14. The actuator 13 depicted here in FIG. 8 is larger than the embodiment of the actuator 13 depicted in FIG. 1. As such, the tip 12 can connect directly to the larger actuator 13.

Figure 9:
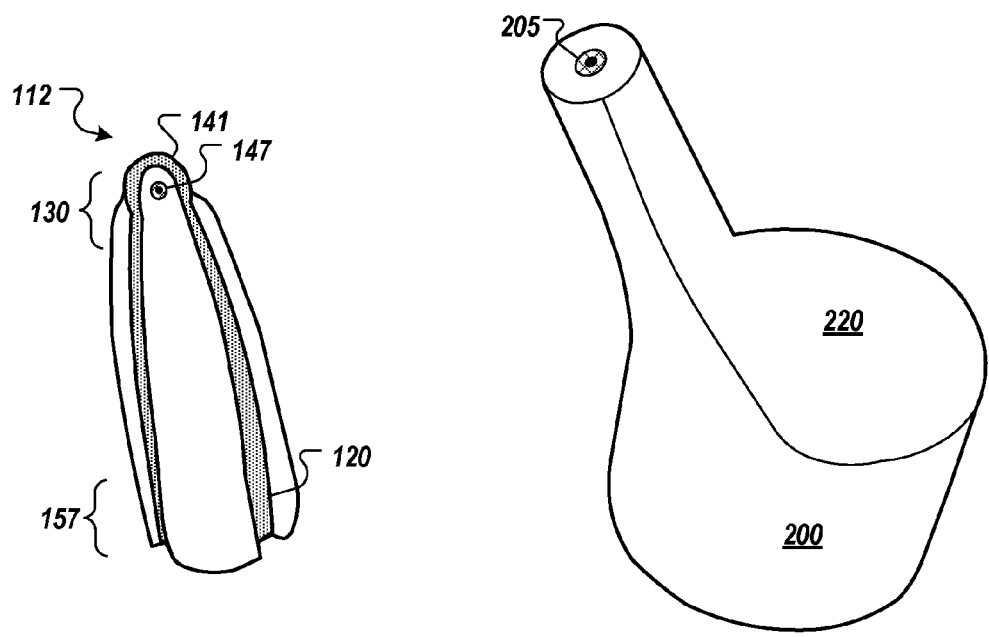
FIG. 9 is a perspective view of an implementation of a tip and actuator.
Figure 10:
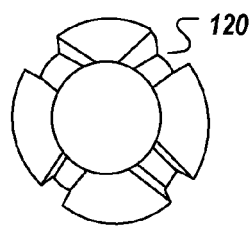
FIG. 10 is a top view of an implementation of a tip.

Referring to FIGS. 9 and 10, in some implementations, the tip 112 is approximately conically shaped from top to bottom. The tip 112 can have a base 157 with a circular inner diameter and an outer diameter that is either circular or approximately circular. Thus, the tip has an internal channel extending from the base 157 to an end upper region 130 of the tip 112. The tip 112 can include one or more grooves 120, such as two, three, four, five or six grooves. The grooves 120 can extend from the base 157 to the upper region 130 of the tip 112. In some implementations, the grooves extend at least 80% of the length of the tip 112. The tip has a thickness in the grooved area that is less than the thickness in the non-grooved area. Therefore, the grooved area can be more flexible than the non-grooved areas and can stretch more in a lateral direction, the lateral direction being perpendicular to the long axis of the internal channel, than the non-grooved areas.

Figure 11:
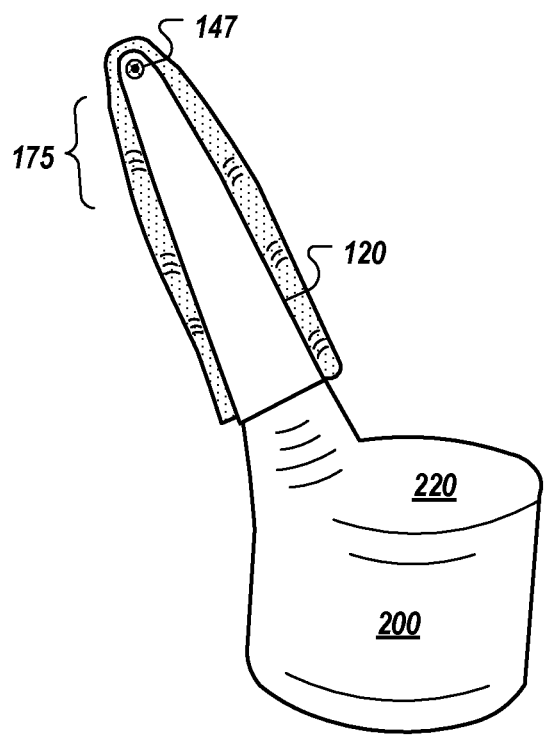
FIG. 11 is a side view of a tip on an actuator.

Referring to FIGS. 9 and 11, in some implementations, the upper region 130 of the tip has a smooth curved end 141. The upper region 130 of the tip can have one or more apertures 147 extending from the interior channel to the outer surface of the tip 112. In some implementations, the apertures 147 are not in the end 141, but are just below the end 141 and on the sides of the end 141. In some implementations, the apertures 147 are aligned with the thick portions of the tip 157 and not with the grooves 120. In some implementations, the tip 112 includes two apertures 147, each one directly across from one another so that the channel and the apertures together form a T-shape.

As with the first described tip, this tip can be formed of a flexible material, such as silicone or some another soft, flexible material (e.g., plastic, rubber, non-permeable cloth, etc.) that can generally feel comfortable against the user's skin. The actuator can be formed of a material that is significantly more rigid than the tip 112. As such, the actuator can hold its shape during use.

The tip 112 can fit over an actuator 200. The actuator can be similar to or the same as the actuator shown in FIG. 9. The actuator 200 has aperture 205 in its upper end. The aperture 205 is fluidly connected to a channel that extends the length of the actuator 200. The actuator 200 has a flat region 220 for depressing the actuator 200 and causing it to actuate a valve to which the channel is fluidly connected. The aperture 205 in the end of the actuator can be small, such as between 0.2 and 1 mm, e.g., around 0.4-0.6 mm in diameter. In some implementations, the aperture 205 in the actuator 200 is smaller than the apertures 147 in the tip 112.

Because of the flexibility of the tip 112, the tip can fit snugly around an end of the actuator. In some implementations, the snug fit is all around the circumference of the actuator. Thus, a liquid tight fit can be achieved around the actuator. In some implementations, at least 25%, such as at least 50%, for example, more than 60% of the tip length is over the actuator. This can prevent the tip from being pushed off of the actuator by the fluid pressure coming out of the dispenser. The shape of the actuator can be wider at the base than the tip. In some implementations, the tip has a cylindrical portion at a distal end, which transitions into widening portion that extends to the base. Because the tip can be flexible and stretch, the width of the tip can be equal to or smaller than the width of the actuator when the tip is not stretched or is in a relaxed state.

Between the end of the actuator and the apertures in the tip the channel forms a pocket 175 where fluid can pool before being pushed out of the apertures. The pocket 175 can have a length of between about 0.5 and 1.5 cm, such as around 1 cm. The pocket diameter can be between 0.2 and 0.6 cm.

In some implementations, the external diameter of the tip 112 at its base 157 is between 0.8 and 1.4 cm, such as between 0.9 and 1.2 cm. The thick regions of the tip 112 at the base 157 can be between 0.7 and 2 mm, such as around 1.7 mm. The thin regions, that is, the regions with the grooves, can be between 0.5 and 1 mm, such as about 0.7 or 0.8 mm. The length of the tip 112 can be between 2 and 5 cm, such as about 4 cm. The end of the tip 141 can be between 0.2 and 0.6 cm wide, such as about 0.4 cm. The apertures 147 can have a diameter of between about 0.6 and 1.5 mm, such as around 1 mm. The apertures 147 can be circular in shape.

Unlike the tip shown in FIG. 8, the tip with the apertures on a side surface of the tip causes fluid to exit the tip at approximately a right angle to the longest length of the tip.

During use of the fluid ejection device, a user can partially insert the tip into a nasal cavity. The fluid ejection device can be held, for example, is in the upright position, where the tip is generally above the body. Controlling the flow of fluid from the tip can be accomplished, for example, by pressing a flat-shaped button area, operable to engage (or disengage) the valve (not shown) inside the actuator when the button area is pressed (or released). This fashion of controlling fluid flow differs from that described with respect to FIG. 1 in which the entire tip can be pressed. In FIG. 1, fluid flow can be controlled, for example, by pressing downwardly or at an angle to a longitudinal axis of the tip. In some implementations, the tip can be pressed straight against the nose so that the actuator is effectively depressed, allowing the valve to open and fluid to flow from the tip. In some implementations, such as those shown in FIG. 8, the actuator can be depressed, such as with a finger, to cause solution to exit the tip. In other implementations, pressing the tip from the side actuates the valve and causes the fluid flow into the tip. Other implementations can include other controls, such as switches, levers, or electronic controls capable of opening and closing the valve. In some implementations, an additional control or button may exist that allows the valve to be locked in the open position. The tip can provide a gentler and more comfortable rinsing experience for a user.

A number of embodiments of the invention have been described. Nevertheless, it will be understood that various modifications may be made without departing from the spirit and scope of the invention. For example, instead of attenuating a fast stream of liquid into a gentle flow, a mist exiting the actuator can be transformed into a gentle cleansing stream of fluid. Accordingly, other embodiments are within the scope of the following claims.

What is claimed is:

1. A device comprising:
a body surrounding a chamber;
a valve;
an actuator having a fluid path that is fluidly connected to the chamber when the valve is in an open position; and
a tip, wherein the tip is configured to attenuate a pressure of fluid flow exiting the actuator,
wherein the tip has a distal portion and a proximate portion, the distal portion has a stop and an aperture wherein the aperture is centrally disposed at a top of the tip, the stop being positioned to block the fluid flow from directly exiting the aperture when dispensed from the actuator and causing the fluid flow to be redirected toward the proximate portion of the tip and wherein the distal portion includes at least four apertures and the at least four apertures surround the stop.

2. The device of claim 1, wherein an exterior of the tip tapers outwardly between the distal portion and the proximate portion.

3. The device of claim 2, wherein the exterior is curved between the distal portion and the proximate portion.

4. The device of claim 1, wherein the aperture in the distal proximate portion defines an interior of a collar that surrounds a portion of the actuator.

5. The device of claim 1, wherein
a canal is between the at least four apertures and the aperture that defines the interior of the collar; and
each of the four apertures is fluidly connected to an annular chamber, and the annular chamber is fluidly connected to the canal.

6. The device of claim 5, wherein a greatest extent of the at least four apertures together is greater than an external circumference of the annular chamber.

7. The device of claim 6, further comprising a circular chamber between the canal and the annular chamber.

8. The device of claim 7, wherein the external circumference of the annular chamber is greater than a circumference of the circular chamber.

9. The device of claim 8, wherein the circumference of the circular chamber is less than a minimum circumference of the canal by at least 0.1 mm.

10. The device of claim 9, wherein the canal has an internal volume of at least 0.47 cm$^3$.

11. A device, comprising:
a body surrounding a chamber, wherein the body is configured to resist a change in shape when a pressure change occurs within the body;
a valve;
an actuator having a fluid path that is fluidly connected to the chamber when the valve is in an open position; and
a tip, wherein the tip is configured to attenuate a pressure of fluid flow exiting the actuator, the tip including an aperture that is centrally disposed at a top of the tip and a stop that redirects fluid back into the chamber so as to facilitate the attenuation of pressure when fluid exits the actuator and inhibit fluid from directly exiting the aperture when the actuator valve is open and wherein the distal portion includes at least four apertures and the at least four apertures surround the stop.

12. The device of claim 11, further comprising a tube within the chamber and connected to the valve.

13. The device of claim 12, further comprising a bag, wherein the bag comprises a flexible material, is within the body, and surrounds the tube and an interior of the bag is hermetically sealed from a space between the body and an exterior of the bag.

14. The device of claim 11, wherein the tip is formed of a flexible material.

15. The device of claim 14, wherein the tip is formed of silicone.

16. The device of claim 14, wherein the actuator is formed of a material that is more rigid than the tip.

17. The device of claim 14, wherein the tip has a distal portion and a proximate portion, an aperture in the proximate portion defines an interior of a collar that surrounds a portion of the actuator, wherein the stop of the tip is positioned to block the fluid flow exiting the aperture and causes the fluid flow to be redirected toward the proximate portion of the tip that allows fluid to be accumulated inside the tip and dispensed at the attenuated pressure through the at least four apertures.

18. The device of claim 17, wherein the tip has an exterior circumference of less than 1.5 cm.

19. The device of claim 14, wherein the tip has one or more grooves extending from an open proximal portion and at least 50% of a length of the tip.

20. The device of claim 19, wherein the tip has an aperture along a side surface of the tip that is fluidly connected to an interior channel extending from the open proximal portion.

21. The device of claim 20, wherein the tip has two apertures across from one another, the apertures and the interior channel configured in the shape of a T.

22. The device of claim 11, wherein the tip includes a flat surface, the flat surface having the at least four apertures thereon to facilitate dispensing of fluid from the body.

23. The device of claim 22, wherein the tip includes a distal portion that tapers outwardly from the flat surface to a proximate portion.

24. The device of claim 23, wherein the proximate portion defines an interior boundary that secures to a portion of the actuator.

25. The device of claim 11, wherein the tip is configured to fit over a portion of an extended end of the actuator, the extended end extending from an upper surface of the actuator.

26. The device of claim 25, wherein the valve is actuated in the open position upon asserting pressure to the upper surface of the actuator.

* * * * *

UNITED STATES PATENT AND TRADEMARK OFFICE
CERTIFICATE OF CORRECTION

PATENT NO.         : 8,834,433 B2                                                       Page 1 of 1
APPLICATION NO.    : 13/708681
DATED              : September 16, 2014
INVENTOR(S)        : Ketan C. Mehta It is certified that error appears in the above-identified patent and that said Letters Patent is hereby corrected as shown below:

In the claims

Column 9, line 49, Claim 4: delete "the distal" and insert --the--.

Signed and Sealed this
Twenty-third Day of December, 2014

Michelle K. Lee
*Deputy Director of the United States Patent and Trademark Office*